(12) United States Patent
Wu

(10) Patent No.: US 7,341,745 B2
(45) Date of Patent: Mar. 11, 2008

(54) METHOD FOR DECREASING NICOTINE AND OTHER SUBSTANCE USE IN HUMANS

(75) Inventor: Jie Wu, Avondale, AZ (US)

(73) Assignee: Arizona Health Consulting, LLC, Scottsdale, AZ (US)

( * ) Notice: Subject to any disclaimer, the term of this patent is extended or adjusted under 35 U.S.C. 154(b) by 0 days.

(21) Appl. No.: 10/360,112

(22) Filed: Feb. 7, 2003

(65) Prior Publication Data

US 2004/0156932 A1    Aug. 12, 2004

(51) Int. Cl.
*A61K 36/00* (2006.01)

(52) U.S. Cl. .................. 424/725; 424/773; 424/774; 424/779

(58) Field of Classification Search ............... 424/725; 514/279, 289, 810, 813
See application file for complete search history.

(56) References Cited

U.S. PATENT DOCUMENTS

| | | | |
|---|---|---|---|
| 3,843,788 A * | 10/1974 | Iwasa et al. ................. | 424/773 |
| 4,517,172 A | 5/1985 | Southard | |
| 4,590,061 A | 5/1986 | Southard | |
| 4,767,861 A | 8/1988 | Boulware | |
| 4,818,533 A | 4/1989 | Boulware et al. | |
| 5,242,926 A | 9/1993 | Hsieh et al. | |
| 5,308,619 A | 5/1994 | Schneider et al. | |
| 5,411,733 A | 5/1995 | Hozumi et al. | |
| 5,417,979 A | 5/1995 | Fan et al. | |
| 5,547,956 A * | 8/1996 | Qu et al. | |
| 5,616,324 A | 4/1997 | Foster et al. | |
| 5,876,728 A | 3/1999 | Kass et al. | |
| 6,210,680 B1 | 4/2001 | Jia et al. | |
| 6,217,880 B1 | 4/2001 | Lan | |
| 6,239,139 B1 | 5/2001 | Kim et al. | |
| 6,255,317 B1 | 7/2001 | Kim et al. | |
| 6,933,291 B2 * | 8/2005 | Qi et al. ...................... | 514/171 |
| 2001/0000731 A1 | 5/2001 | Jia et al. | |
| 2001/0038863 A1* | 11/2001 | Jaenicke et al. ............ | 424/725 |
| 2002/0031559 A1 | 3/2002 | Liang et al. | |
| 2002/0038863 A1 | 4/2002 | Walker | |
| 2002/0039587 A1 | 4/2002 | Tao | |
| 2002/0041906 A1 | 4/2002 | Tao | |
| 2002/0068095 A1 | 6/2002 | Qi et al. | |
| 2002/0068097 A1 | 6/2002 | Basu | |

FOREIGN PATENT DOCUMENTS

JP           2000-191530           7/2000

OTHER PUBLICATIONS

Blanchfield et al. (Natural Product Letters (1993), vol. 3, No. 4, pp. 305-312).*

Vetulani (Polish Journal of Pharmacology (2001), vol. 53, pp. 415-434).* www.bioimages.org.uk/HTML/T79.HTM; accessed Apr. 21, 2004.*

Pan et al. (Yiyao Gongye (1988), vol. 19, No. 7, pp. 319-320).*

Zhang et al. (Life Sciences (1998), vol. 63, No. 7, pp. 537-544).*

Jie Wu, Guo-Zhang Jin, "Tetrahydroberberine suppresses dopamine-induced potassium current in acutely dissociated CA1 pyramidal neurons from rat hippocampus," *Neuroscience Letters* 207 (1996), pp. 155-158.

Jie Wu, Guo Zhang Jin, "Tetrahydroberberine inhibits acetylcholine-induced K⁺ current in acutely dissociated rat hippocampal CA1 pyramidal neurons,"*Neuroscience Letters* 222 (1997), pp. 115-118.

Jie Wu, Guo Zhang Jin, "Tetrahydroberberine blocks membrane K⁺ channels underlying its inhibition of intracellular message-mediated outward currents in acutely dissociated CA1 neurons from rat hippocampus," *Brain Research* 775 (1997), pp. 214-218.

Masayuki Niwa, Iiiroyuki Mibu, Masakatsu Nozaki, Kaito Tsurumi, Hajime Fujimura, "Dopaminergic Unique Affinity of Tetrahydroberberine and 1-Tetrahydroberberine-d-Camphor Sulfonate," *Pharmacology* 1991, pp. 329-336.

(Continued)

*Primary Examiner*—Susan Coe Hoffman
(74) *Attorney, Agent, or Firm*—Robert D. Atkins; Quarles & Brady LLP

(57) ABSTRACT

A method for decreasing nicotine and other substance use in humans is disclosed. Tetrahydroberberine (THB) and its analogs, 1-Tetrahydropalmatine (1-THP) and 1-Stepholidine (1-SPD), are present in and can be isolated from several plants in the Magnoliidae superorder. According to the disclosed method, THB and its analogs are used to block nicotine-induced DA release, and modulate heterologous or homoeric expression of human nicotinic acetylcholine receptors (nAChR) in humans. Specifically, THB exhibits bi-directory modulation of α4β2-nAChR-mediated currents induced by nicotine. THB also shows predominant inhibition on homologously expressed α7-nAChR function. Thus, according to the disclosed method, THB is used to simultaneous blockade midbrain DA system function, the brain reward center, and neuronal α4β2- and α7-nAChR function, the major nicotine targets in the brain. Therefore, THB and its analogs serve as a novel class of natural compounds to decrease nicotine dependence in humans. Furthermore other substances, such as alcohol, cocaine, and opiates, also operate by triggering the brain reward center, resulting in a cycle of substance or alcohol abuse. THB and its analogs can be used to decrease use of substances such as alcohol, cocaine, and opiates. Finally, because THB and its analogs are DA antagonists, THB and its analogs can also be used as a treatment for Parkinson's Disease, Alzheimer's Disease and Schizophrenia.

18 Claims, 8 Drawing Sheets

OTHER PUBLICATIONS

Iwasa K, Nanba H, Lee Du, Kang Si, "Structure-activity relationships of protoberberines having antimicrobial activity," NCBI, *National Library of Medicine*, Abstract of Planta Medica (1998) vol. 64, No. 8, pp. 748-751.

Sheng WD, Jiddawi MS, Hong XQ, Abdulla SM, "Treatment of chloroquine-resistant malaria using pyrimethamine in combination with berberine, tetracycline or cotrimoxazole," NCBI, *National library of medicine*, Abstract of East Afr. Med. J. (1997) vol. 74, No. 5, pp. 283-284.

"A Randomized Controlled Trial of the Use of Craniosacral Osteopathic Manipulative Treatment and of Botanical Treatment in Recurrent otitis media in Children," ClinicalTrials.gov, Jul. 2002.

* cited by examiner

A. Tetrahydroberberine (THB)

B. *l*-Tetrahydropalmatine (*l*-THP)

C. *l*-Stepholidine (*l*-SPD)

US 7,341,745 B2

METHOD FOR DECREASING NICOTINE AND OTHER SUBSTANCE USE IN HUMANS

FIELD OF THE INVENTION

The present invention relates generally to a method for decreasing human's cravings for cigarettes and reducing instances of relapse during detoxification once smoking abstinence has been achieved, and more specifically, to a method for decreasing nicotine use by treating a human with a novel class of natural compounds such as tetrahydroberberine (THB) and its analogs, isolated from the Magnoliidae superorder of plants, such as *Corydalis* and *Stephania*.

BACKGROUND OF THE INVENTION

Cigarette smoking is a prevalent, modifiable risk factor for increased morbidity and mortality in the United States, and perhaps in the world. Smokers incur medical risks attributable to direct inhalation. Bystanders, termed passive smokers, also incur medical risks from second-hand smoke. Society, as a whole, also bears the economic costs associated with death and disease attributable to smoking. Although the majority of smokers have tried repeatedly to quit smoking, eighty percent of smokers return to tobacco in less than two years after quitting. Therefore, tobacco dependence is a health hazard for millions of Americans.

Nicotine is the principal alkaloid in tobacco and is primarily responsible for tobacco dependence. The initiation and maintenance of tobacco dependence in a human is due to certain bio-behavioral and neuromolecular mechanisms. Nicotinic acetylcholine receptors (nAChRs) in humans are the initial binding sites for nicotine. The binding of nicotine to nAChRs modulates the brain's "reward" function by triggering dopamine release in the human brain.

Although a variety of psychopharmacological effects contribute to the reinforcing action, the existence of a mesolimbic dopaminergic pathway for nicotinic reward is the predominant hypothesis. The mesolimbic dopaminergic pathway originates in the ventral tegmental area (VTA) of the midbrain and projects to forebrain structures including the prefrontal cortex and to limbic areas such as the olfactory tubercle, the amygdala, the septal region, and the nucleus accumbens. Many studies have indicated that dopamine release in the nucleus accumbens of the human brain is "rewarding" or signals an encounter with a "reward" from the environment. Other substances, such as alcohol, cocaine, and opiates, operate in the same manner, resulting in a cycle of substance or alcohol abuse.

Therefore, a need exists for a novel compound that can block the dopamine release system to abolish nicotinic stimulation or smoking-induced "rewarding" and/or can block nAChRs to limit increasing nicotine-induced dopamine release.

SUMMARY OF THE INVENTION

The present invention provides a method for decreasing nicotine use in living organisms, for example, in humans. In one embodiment, and by way of example only, the method includes administering a dose of Magnoliidae to the living organism providing at least one Magnoliidae compound, selected from the group Tetrahydraberberine (THB), Tetrahydropalmatine (l-THP) and Stepholidine (l-SPD), in an effective amount to reduce nicotine use by the living organism. The dose of Magnoliidae can be administered, for example, orally, sublingually, dermally, subcutaneously, intravenously or through respiratory inhalation.

In another exemplary embodiment, a method for reducing sensitization to nicotine in a living organism includes administering a dose of THB, l-THP, l-SPD, or analogs of THB, following extraction from one or more Magnoliidae plants. In one embodiment, and by way of example only, THB analogs include a conserved four-ring structure, that in another example, include a benzene-hexane-hexane-benzene structure.

Other independent features and advantages of the method for decreasing nicotine use in living organisms will become apparent from the following detailed description, taken in conjunction with the accompanying drawings which illustrate, by way of example, the principles of the invention.

DETAILED DESCRIPTION OF VARIOUS EMBODIMENTS

This description discloses a method for reducing smoking in humans by treating a human with one of a group of chemical analogs isolated from select genera of the Magnoliidae superorder of plants.

Figure 1:
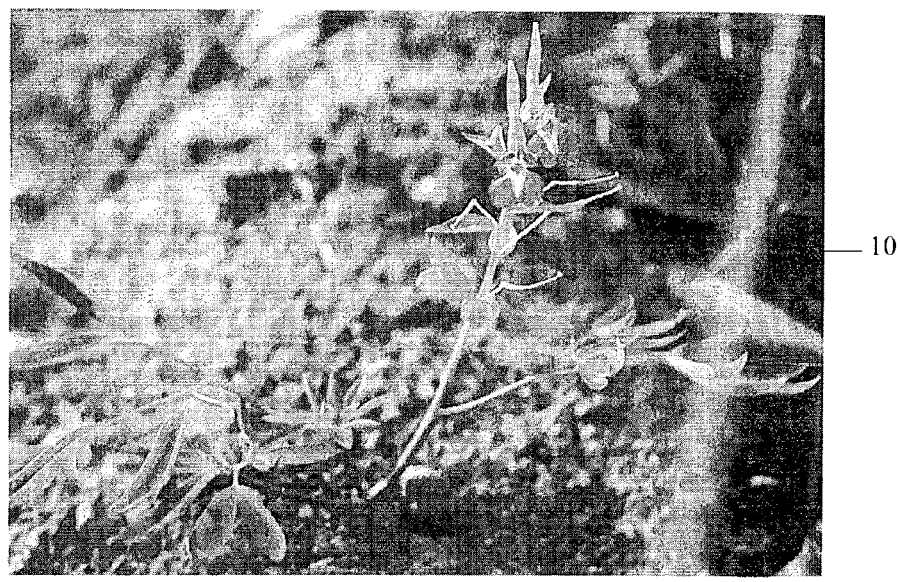
FIG. 1 is an illustration of a *Corydalis ambigua* plant.

FIG. 1 is an illustration of one species of *Corydalis*, specifically, *Corydalis ambigua* 10. *Corydalis ambigua* 10 is one species of the *Corydalis* genus of herbal plants, primarily found in East Asia, namely China, and Japan. Mature *Corydalis ambigua* 10 is about 150.0 cm in height and about 80.0 cm in width. *Corydalis ambigua* 10 is a perennial herb. *Corydalis* is a genus of the Fumariaceae sub-family, the Papoveraceae family, the Papaverales order and the Magnoliidae superorder of plants.

Figure 2:
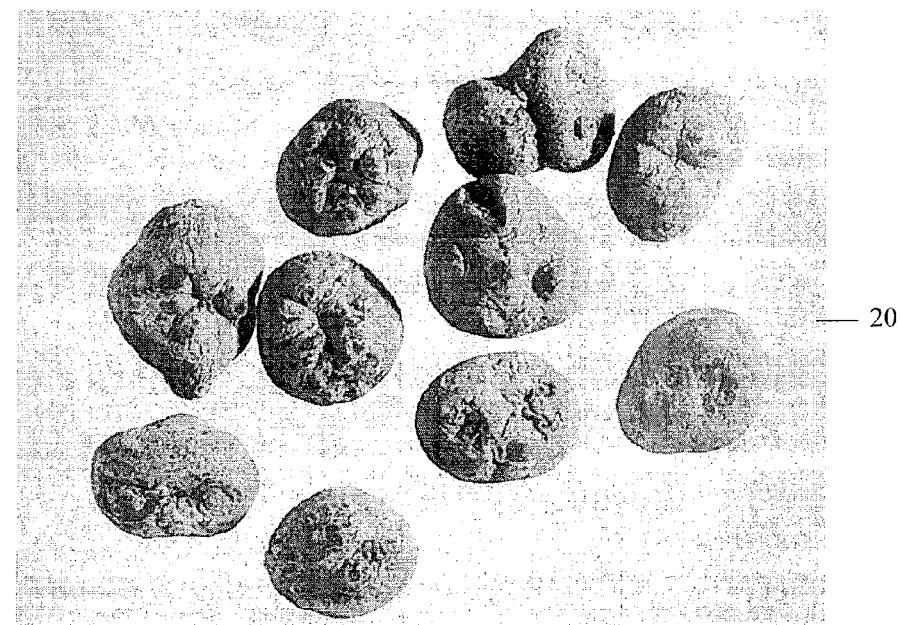
FIG. 2 is an illustration of tubers from the *Corydalis ambigua* plant.

FIG. 2 is a depiction of the tubers 20 of the *Corydalis ambigua* plant. While one embodiment specifically refers to using the *ambigua* species, any species of *Corydalis* containing tetrahydroberberine (THB) or its analogs may be used. Thus, the term *Corydalis* refers to all species of *Corydalis* containing THB or its analogs, including *Corydalis ambigua*. Although, one embodiment specifically envisions extracting THB and its analogs from the tubers 20 of the *Corydalis ambigua*, THB and its analogs can be extracted by purifying any of the plant parts, including, but not limited to, the leaves, stem, and tubers. Furthermore, a second embodiment envisions administering *Corydalis*, without prior purification of THB or its analogs. Thus, the term *Corydalis* encompasses the entire *Corydalis* plant and also all extracts derived from the *Corydalis* plant.

Figure 3:
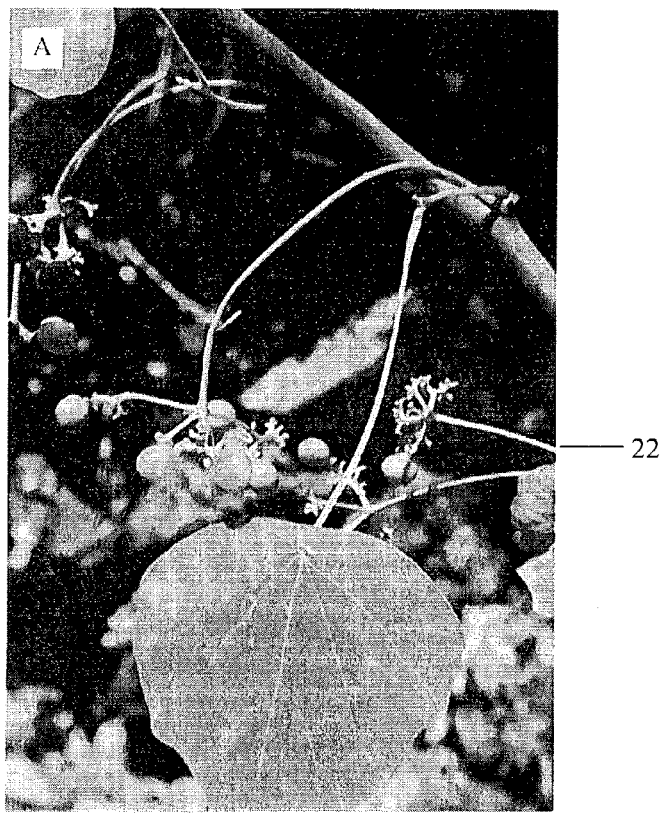
FIG. 3 are illustrations of a *Stephania* plant and tubers from the *Stephania* plant.
Figure 3:
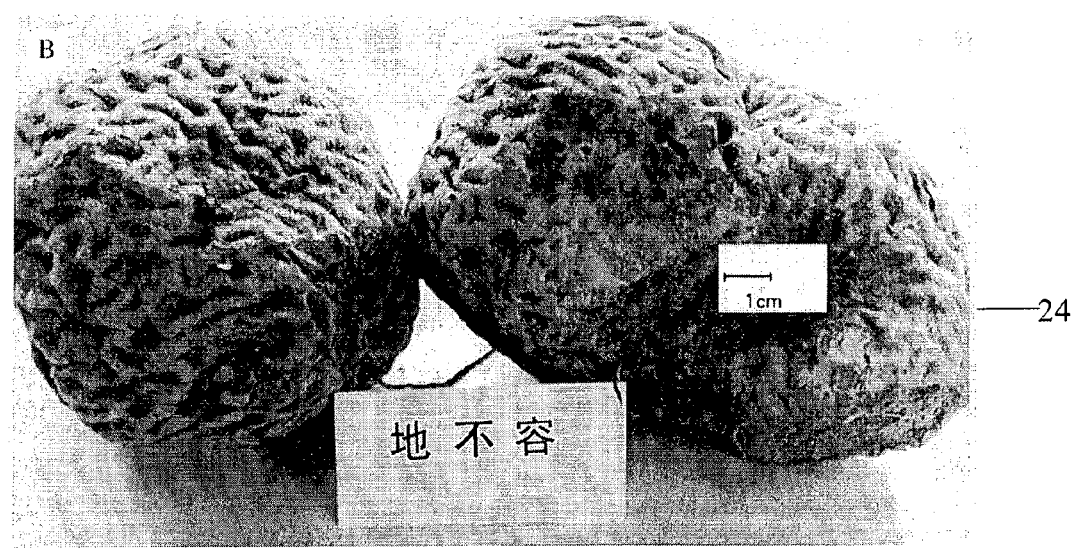

FIG. 3A is an illustration of one species of the *Stephania* genus of plants, also a genus of herbal plants, primarily found in East Asia. FIG. 3B is a depiction of the tubers of the *Stephania* plant. The *Stephania* genus of plants includes, but is not limited to, *Stephania intermedia, Stephania hainanensis*, and *Stephania yunnanensis*. The *Stephania* genus of plants contains analogs of THB. Specifically, *Stephania intermedia, hainanensis*, and *yunnanensis* contain l-tetrahydropalmatine (l-THP or dl-THP) while both *Stephania intermedia* and *yunnanensis* contain l-Stepholidine (l-SPD). L-THP can also be found in and purified from *Fibraurea recisa Pierre*. Both *Stephania* and *Fibraurea* are from the Menispermaceae family and Ranunculales order of plants. As with *Corydalis*, both *Stephania* and *Fibraurea* belong to the Magnoliidae superorder of plants.

As with *Corydalis*, one embodiment specifically envisions extracting l-THP and l-SPD from the tubers of the *Fibraurea* or *Stephania* plants. However, in a second embodiment, l-THP and l-SPD can be extracted by purifying any of the plant parts, including, but not limited to, the leaves, stem, and tubers. Yet another embodiment envisions administering any species of *Stephania* or *Fibraurea* without prior purification of l-THP or l-SPD.

According to the present disclosure, the term Magnoliidae will be used to refer to all species in the Magnoliidae superorder of plants that contain THB, l-THP, l-SPD, or any analog of THB, l-THP, or l-SPD. FIGS. 4A-C show the chemical structure of compounds 30 isolated from Magnoliidae plants. According to one embodiment, compounds 30 can be referred to collectively as "Magnoliidae compounds" or each, singularly, as "a Magnoliidae compound." However, according to one embodiment, Magnoliidae compounds are not limited to the Magnoliidae compounds 30 shown, but also include any analog of Magnoliidae compounds 30. In one embodiment, analog of Magnoliidae compounds 30 can be characterized by a conserved four-ring structure. For example, the analogs can have a conserved benzene-hexane-hexane-benzene structure, as shown in all Magnoliidae compounds 30.

FIG. 4A shows the chemical structure of Tetrahydroberberine (THB) 32. FIG. 4B shows the chemical structure of one analog of THB 32, l-Tetrahydropalmatine (l-THP) 34. FIG. 4C shows the chemical structure of a second analog of THB 32, l-Stepholidine (l-SPD) 36. l-THP 34 and l-SPD 36 are homologue analogs of THB and are collectively referred to as THB analogs. Magnoliidae compounds 30 are extracted from one or more parts of any Magnoliidae species by Classical Alkaloid Chemical Purifying Method. In one embodiment, the Magnoliidae plant is immersed into an alkaline solution, extracted using benzene, then crystallized and purified to get THB 32, l-THP 34, and l-SPD 36. In another embodiment, if Magnoliidae compounds are not practically available as found in or extracted from Magnoliidae plants, Magnoliidae compounds may be synthesized or derived from other sources.

Magnoliidae compounds exhibit a marked depression effect in the central nervous system such as sedation, hypnosis and analgesia. The pharmacological mechanism of THB and its analogs involve working as a class of antagonists to inhibit brain dopamine receptor (DA) function, blockade of α-adrenergic receptor and 5-TH receptor functions, and direct modulation of ion channel function.

Numerous biochemical and behavioral experiments have indicated that THB and its analogs exhibit all the characteristics of a DA antagonist. Compared with traditional DA receptor antagonists, the Magnoliidae compounds exhibit two unique properties. First, THB possesses an equipotent effect on D1-type and D2-type DA receptor binding. Second, in normal rats, l-SPD exhibits the characteristics of D2 receptor antagonist, while in rats with unilateral nigral lesion (DA receptor super sensitivity in striatum), l-SPD acts on D1 receptors as an agonist. Therefore, by blocking DA receptor function, Magnoliidae compounds block nicotine-induced DA release, which is the major cellular mechanism of nicotine reward and dependence.

Basic cellular mechanisms of nicotinic dependence also involve the functional state changes during repeated nicotinic agonists exposure and receptor changes in the number of receptors during chronic nicotinic exposure. Nicotinic Acetylcholine Receptors (nAChRs) can exist in many different functional states, such as resting, activation, desensitization or inactivation. The desensitization of nAChRs plays an important role in initiating nicotinic tolerance and dependence. Recovery from receptor desensitization contributes to nicotinic withdrawal symptoms.

Magnoliidae compounds possess clear modulating effects on heterologous expression of human nicotinic acetylcholine receptors (nAChRs) in the native nAChR-null SH-EP1 human epithelial cell line using patch-clamp techniques. nAChRs are prototypical members of the ligand-gated ion channel superfamily of neurotransmitter receptors. nAChRs provide both classical and contemporary models for the establishment of concepts pertaining to mechanisms of drug action, synaptic transmission, and structure and function of transmembrane signaling compounds.

The nAChRs that mediate depolarizing inward sodium ($Na^+$) current play important roles in classical excitatory neurotransmission at the nerve-muscle junction, through autonomic ganglia, and perhaps in a variety of central nervous system cholinergic pathways that contribute to processes such as perception, cognition, and emotion. nAChRs on nerve terminals also exist on motor, preganglionic and central neurons, and these nAChRs can regulate release of acetylcholine (ACh) or other neurotransmitters, meaning that some nAChRs also modulate neurotransmissions.

nAChRs exist as a diverse family of proteins composed of different combinations of subunits derived from at least seventeen different genes ($α1-α10$, $β1-β4$, $γ$, $δ$, and $ε$). Naturally expressed nAChRs in muscle are made from $α1$, $β1$ $δ$ and either $γ$ (in fetal tissue) or $ε$ (in adult tissue) subunits and have properties just like those of heterologously expressed nAChR made of the same subunits. nAChR can form as homomers of the most ancient subunits, $α7$, $α8$, $α9$ or $α10$, although $α7$ plus $α8$, $α9$ plus $α10$, and other higher order complexes can also form in heterologous expression systems or can also form naturally.

Binary complexes of $α2$, $α3$ $α4$ or $α6$ subunits with $β2$ or $β4$ subunits also can form distinctive nAChR subtypes, at least in heterologous expression systems. $α5$ and $β3$ subunits are likely "wild-cards" able to integrate into at least some of the $α/β$ binary complexes to form ternary complexes with unique properties, and more than one kind of $α$ or $β$ subunit can exist in some nAChR subtypes, for example, naturally expressed $α3α5β2β4$-nAChRs in post-ganglionic neurons and $α4α6β2$-nAChR in heterologous expression systems. Therefore, in one embodiment, heterologous, de novo expression of functional, $α4β2$-nAChR in a cloned epithelial cell line was used to demonstrate the efficacy of Magnoliidae compounds.

Figure 4:
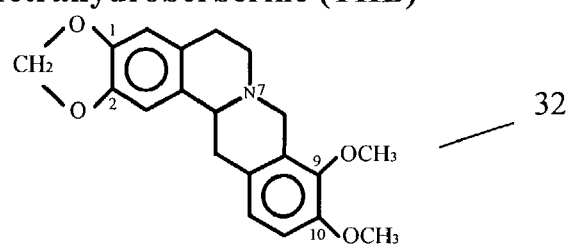
FIG. 4 shows the chemical structure of Tetrahydroberberine (THB) and two analogs of Tetrahydroberberine (THB analogs)
Figure 4:
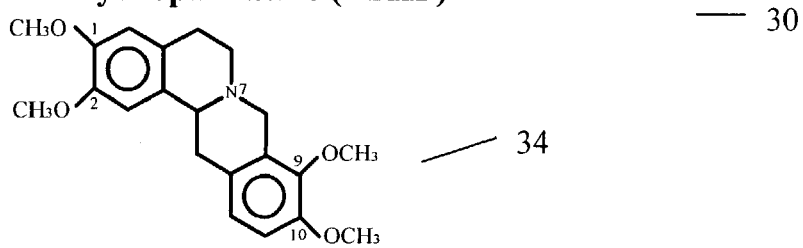
Figure 4:
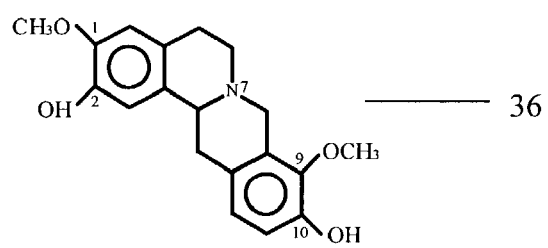
Figure 5:
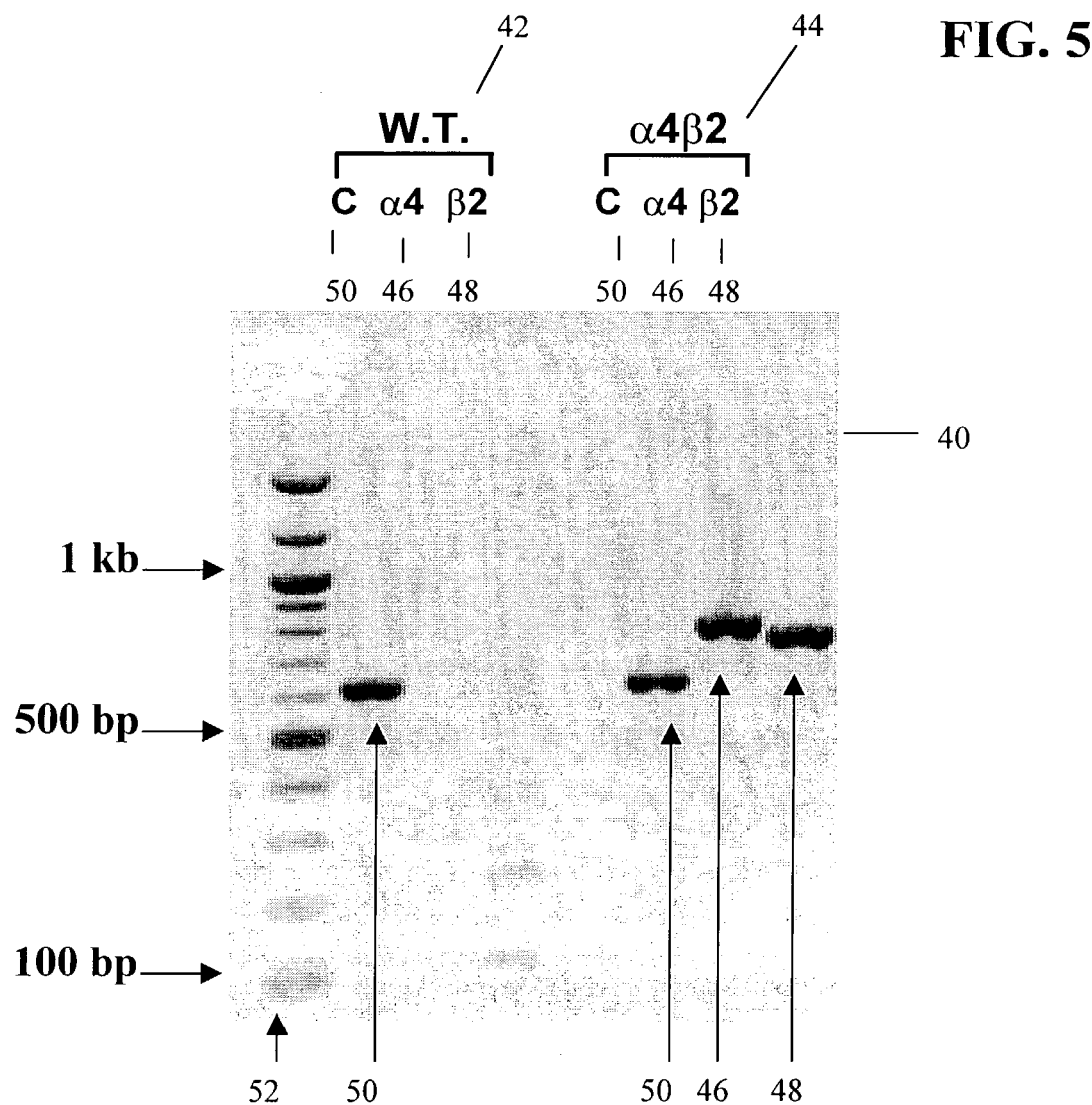
FIG. 5 illustrates the detection of $\alpha 4$ and $\beta 2$ nAChR subunit transcripts by RT-PCR in wild-type SH-EP1 cells and cells co-transfected with $\alpha 4$ and $\beta 2$ cDNA.
Figure 6:
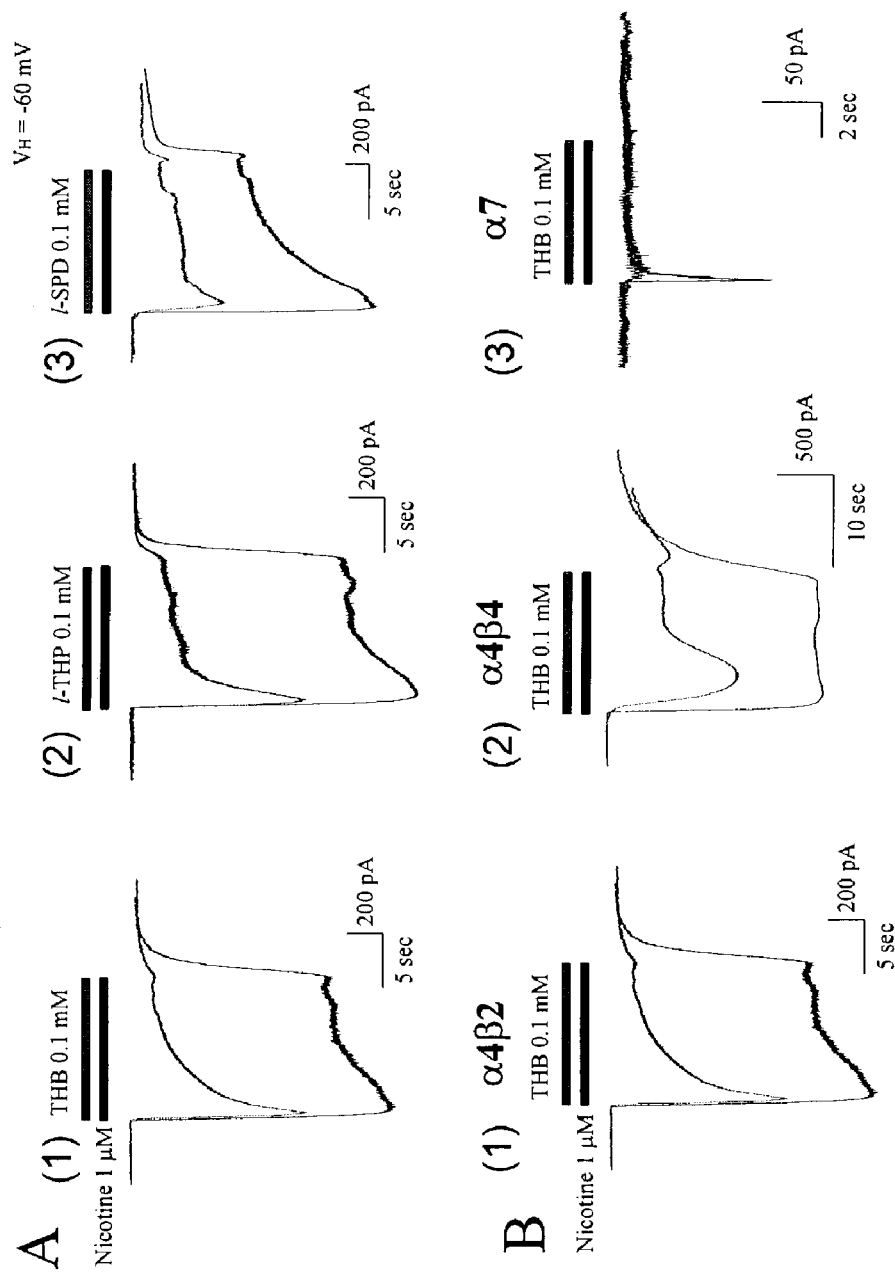
FIG. 6 is a series of graphs illustrating effects of THB and THB analogs on $\alpha 4 \beta 2$-nAChR responses and the effects of THB on nicotinic responses mediated by different nAChR subtypes.
Figure 7:
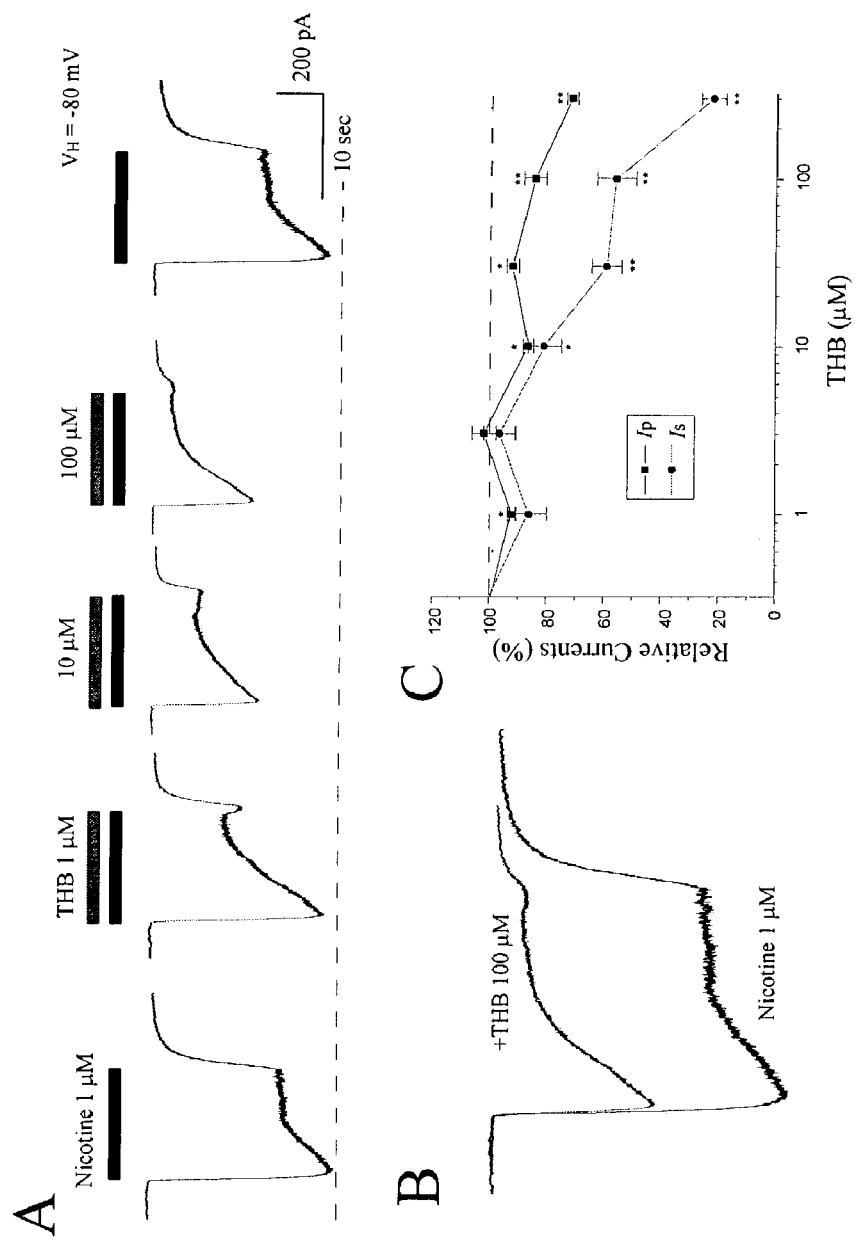
FIG. 7 is a series of graphs illustrating the effects of THB on nicotinic response.

FIG. 5 depicts the detection of α4 and β2 nAchR subunit transcripts by reverse transcription polymerase chain reaction (RT-PCR) in wild-type (WT) human SH-EP1 (nAchR-null human epithelial) cells 42 and human SH-EP1 cells co-transfected with α4 β2 cDNA 44 on an agarose gel 40. In FIG. 4, cDNA was synthesized from 0.8 microgram (μg) of total RNA prepared from wild type SH-EP1, SH-EP1-α4β2, and SH-EP1-α4β4 cells using oligo d(T)$_{12-18}$ primer in a RT reaction. One-tenth of the RT product was then used in each PCR with gene-specific primers for α4 46, β2 48, or GAPDH (lanes C as internal control) 50. One-tenth of each 50 μl RT-PCR product was then resolved on one percent agarose gel. The 100 base pair DNA ladder 52 was used as the molecular weight marker. The presence of α4 46 and β2 48 subunits are seen in the co-transfected cells 44, whereas both are absent in the WT cells 42. Thus, RT-PCR confirms the expression of α4 and β2 nAChR subunits.

In FIGS. 6-9, whole-cell patch-clamp recording techniques in voltage-clamp mode were used to detect changes in current. Conventional whole-cell current recording coupled with techniques for fast application and removal of agonist (9 channel multi-barrel pipette), were applied in this study. Briefly, cells plated on poly-lysine-coated 35-mm culture dishes were placed on the stage of an inverted microscope (Olympus iX7, Lake Success, N.Y.) and continuously superfused with standard external solution (2 ml/min). Glass microelectrodes (3-5 MΩ resistance between pipette and extracellular solutions) were used to form tight seals (>1 GΩ) on the cell surface until suction was applied to convert to conventional whole-cell recording.

Cells were then voltage-clamped at holding potentials of −60 mV and ion currents in response to application of ligands were measured (Axon Instruments 200B amplifier, Foster City, Calif.), typically using data filtered at 2 kHz, acquired at 5 kHz, displayed and digitized on-line (Axon Instruments Digidata 1200 series A/D board), and stored to computer hard drive. Both pipette and whole current capacitance were minimized and the series resistance was routinely compensated to 80%. The access resistance before series resistance compensation was between 10-20 MΩ. Data acquisition and analyses were done using Pclamp8 (Axon Instruments), and results were plotted using Origin 5.0 (Microcal, North Hampton, Mass.).

Data usually were fit over the 10-90% period from inward current peak until agonist exposure was terminated (5-10 sec). The experimental data are presented as means±standard errors, and comparisons of different conditions were analyzed for statistical significance using the Student's t-tests. All experiments were performed at room temperature (22±1° C.). A pipette electrode solution comprising TrisPO$_4$dibasic 110 milli-Molar (mM), Trisbase 28 mM, Ethylenediaminetetraacetate (EDTA) 11 mM, Magnesium Chloride (MgCl$_2$) 2 mM, Calcium Chloride (CaCl$_2$) 0.5 mM, and Sodium-Adenosine Triphosphate (Na-ATP) 4 mM, resulting in a pH of 7.3, was used.

FIG. 6A illustrates the effects of high concentrations of Magnoliidae compounds on α4β2-nAChR responses. The series of graphs illustrate the similar effects of THB (1), l-THP (2) and l-SPD (3), respectively on α2β4-nAChR mediated currents. A concentration of 0.1 mM of each Magnoliidae compound was used. The results demonstrate that each of the Magnoliidae compounds exhibits clear pharmacological effects on human neuronal nAChRs expressed in the human epithelia cell-line. The major pharmacological effect of Magnoliidae compounds at high concentrations is inhibition of nAChR function. In FIG. 6A, the inhibition of nAChR function is represented by the reduction of peak current response and the acceleration of the steady-state component.

In FIG. 6B, the effects of Magnoliidae compounds an nicotinic responses mediated by different nACbR subtypes are shown. In FIG. 6B, the effects of Magnoliidae compounds on α4β2 (1), α4α4 (2) and α7 (3) subtypes is shown. In FIG. 6B, THB, at a concentration of 0.1 mM, was used as the representative Magnoliidae compound. Nicotine, at a concentration of 1.0 μM, was again used as the control. In FIG. 6B, the inhibition of each nAChR subtype function is represented by the reduction of peak current response and the accerleration of the steady-state component. As illustrated in graph (s), the inhibitory effect occurs more predominantly in α7-nAChRs.

FIG. 7A illustrates the concentration-dependent manner in which Magnoliidae compounds effect a nicotinic response in nAChRs. Graphs (1) and (5) illustrate nicotine-induced currents alone, at a concentration of 1.0 μM. Graphs (2), (3), and (4) illustrate the mediating effects of THB when added in the presence of nicotine, as the concentration of THB increases from 1.0 μM (2), to 10 μM (3) to 100 μM (4).

FIG. 7B further illustrates the difference in nicotine-induced currents between nicotine alone and the addition of 100 μM THB. Again, the inhibition of nAChR function is demonstrated by the reduction of peak current response and the acceleration of the steady-state component. FIG. 7C further illustrates this concentration-dependent inhibition as a graphical comparison of peak (Ip) and steady-state (Is) components of nicotinic responses at different THB concentrations.

FIG. 8A illustrates nicotine-induced responses at different nicotine concentrations: 0.1 μM (1), 1.0 μM (2), 10 μM (3), and 100 μM (4). Low nicotine concentrations are representative of the concentration range in the brain of about 100-300 nano-Molar (nM) or 0.1-0.3 μM after one cigarette smoke. FIG. 8B illustrates the effects of THB at a concentration of 30 μM. In FIG. 8A+B, the superimposed graphs of FIGS. 8A and 8B demonstrate the ability of Magnoliidae compounds to modulate α4β2-nAChR function. FIG. 8C shows the dose-response curves of nicotine-induce peak currents with and without THB, while FIG. 8D shows the dose-response curves of nicotine-induced steady-state currents with and without THB.

FIG. 9A and FIG. 9B demonstrate how THB, at a 30 μM concentration, accelerates acute desensitization of nicotine-induced currents at different holding potentials. In FIG. 9A, current-mediation is shown at a holding potential ($V_H$) of −40 milli-Volts (mV). In FIG. 9B, the accelerated acute desensitization is shown t a VH of −80 mV. The bar graph in FIG. 9C compares the relative values for the peak current (Ip), steady state (Is) and decay constant (tau) at two different voltages measured in FIGS. 9A and 9B. Finally, FIG. 9D compares the voltage dependent peak currents without THB (Ip) and in the presence of THB (Ip+THB). FIG. 9D also compares the voltage-dependent steady state currents without THB (Is) and in the presence of THB (Is+THB).

Through the mechanisms described above, Magnoliidae compounds serve to reduce nicotine use and produce smoking cessation in humans through one or more biological mechanisms. First, Magnoliidae compounds act as a DA receptor antagonist, reducing the reward processes in the brain produced by nicotine use. Second, Magnoliidae compounds cause nAChR modulation through bi-directory regulation of nAChR function, specifically through α4β2- nAChR-mediated currents induced by nicotine. At high agonist concentrations, Magnoliidae compounds diminish or even eliminate nAChR function by accelerating nAChR acute desensitization.

At low agonist concentrations, Magnoliidae compounds potentiate nicotinic response or enhance nAChR function. This potentiation may have increased efficacy when combining the Magnoliidae compound with nicotine-replacement therapy (NRT). If Magnoliidae compounds are used together with nicotine (either while still smoking or in conjunction with a nicotine additive or other nicotine-replacement therapy), the Magnoliidae compounds will block the brain reward center function (as the DA receptor antagonists) and reduce the reinforcement feeling, then gradually decrease the human's nicotine-dependence.

$^3$-H nicotine binding experiments demonstrate that Magnoliidae compounds exhibit a low affinity binding ability to α4αβ2-nAChR. At high concentrations, Magnoliidae compounds show more predominant inhibition on heterologously expressed α7-nAChR function. The ability to reduce nicotine use is further illustrated by the ability of Magnoliidae compounds to act on α4β2-nAChR subunits, α4αb4-nAChR subunits, and α7-nAChR subunits.

Further, Magnoliidae compounds may act on α4β2-nAChR subunits combining with any other α or β subunit, including but not limited to α2, α3, α5, α6, or β3. Therefore, the simultaneous blockade of midbrain DA system function (the brain reward center) and neuronal α4β2-nAChR and α7-nAChR function (the major nicotine targets in the brain) by the Magnoliidae compounds, demonstrate that Magnoliidae compounds serve as a novel class of natural compounds for reducing nicotine use and producing smoking cessation in living organisms, particularly in humans.

The nAChRs densensitization, adaptation and up-regulation are the major cellular mechanism of nicotine tolerance, dependence and withdrawal. The major reason to fail in smoking cessation (quitting smoking) is the on-set of nicotine withdrawal symptoms. The basic cellular mechanism for withdrawal symptoms is that the numbers of nAChRs increase in the brain after long term exposure to nicotine. Once a human quits smoking, numerous nAChRs located on brain regions outside of the reward center will activate by an endogenous nicotinic receptor agonist, acetylcholine, and produce a series cardiac, respiratory and endo-secretary responses, called withdrawal symptoms.

Administration of Magnoliidae compounds will eliminate withdrawal symptoms by two mechanisms. First, the Magnoliidae compounds, at low nicotinic concentrations (<500 nM), enhance nAChR efficacy, thus decreasing the required nicotinic concentrations in the brain. Second, the Magnoliidae compounds, at slightly higher nicotinic concentrations (>1.0 μM), diminish nAChR function by acceleration of nAChRs desensitization. Therefore, the optimal way to achieve smoking cessation is to block the brain reward center (DA system) and block the over-expressed nAChR function. Magnoliidae compounds serve both functions and present a novel method to meet these needs, reducing nicotine use and sustaining smoking cessation.

The ability of Magnoliidae compounds to decrease nicotine use is further enhanced by the compounds' ability to act on no-epinephrine, epinephrine, and/or serotonin (5-TH) receptors. Because of the ability of Magnoliidae compounds to act on these receptors as well as acting as a DA receptor antagonist, reducing the reward processes in the brain, Magnoliidae compounds are also useful in treating other substance use, abuse and addiction. Therefore, Magnoliidae compounds can be administered to humans to reduce use of addictive substances, including reducing alcohol, cocaine, and opiate (or opioid) use.

Figure 8:
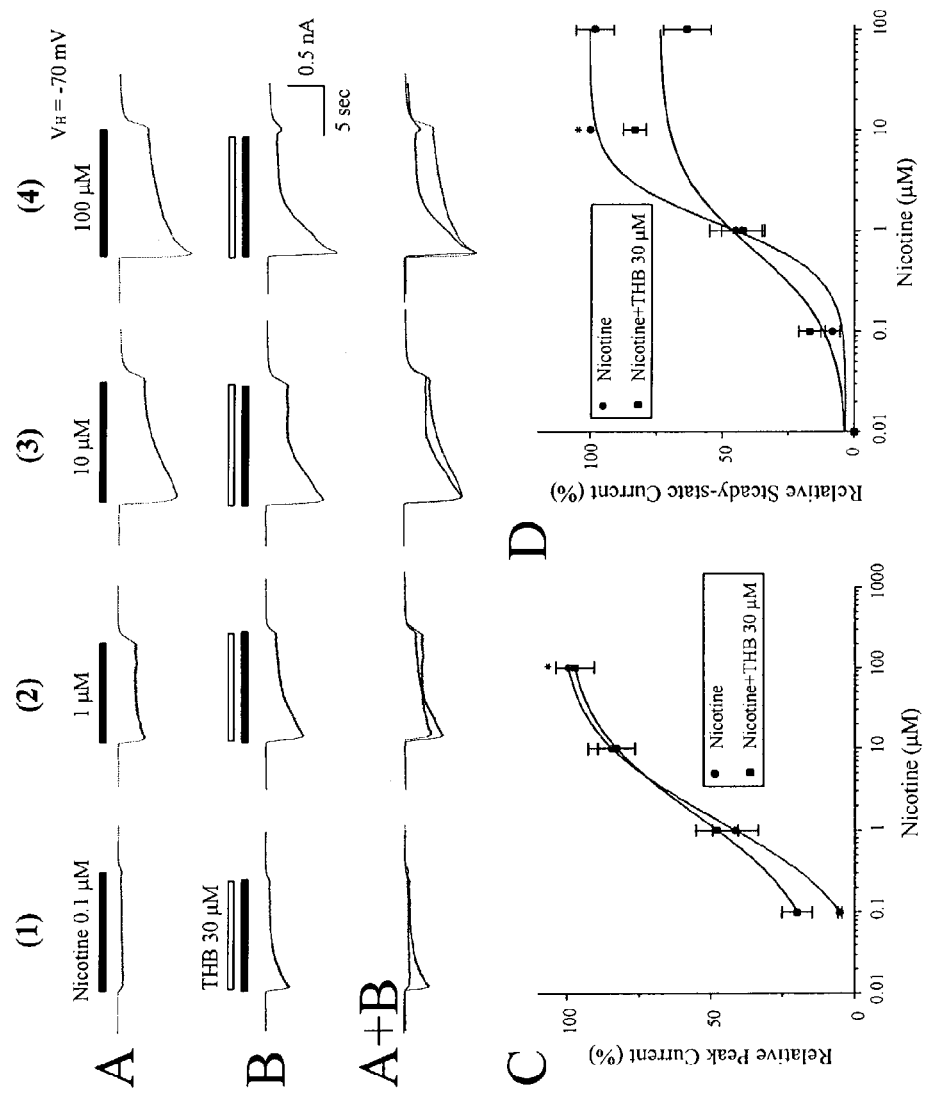
FIG. 8 further illustrates the effects of THB on nicotine responses.
Figure 9:
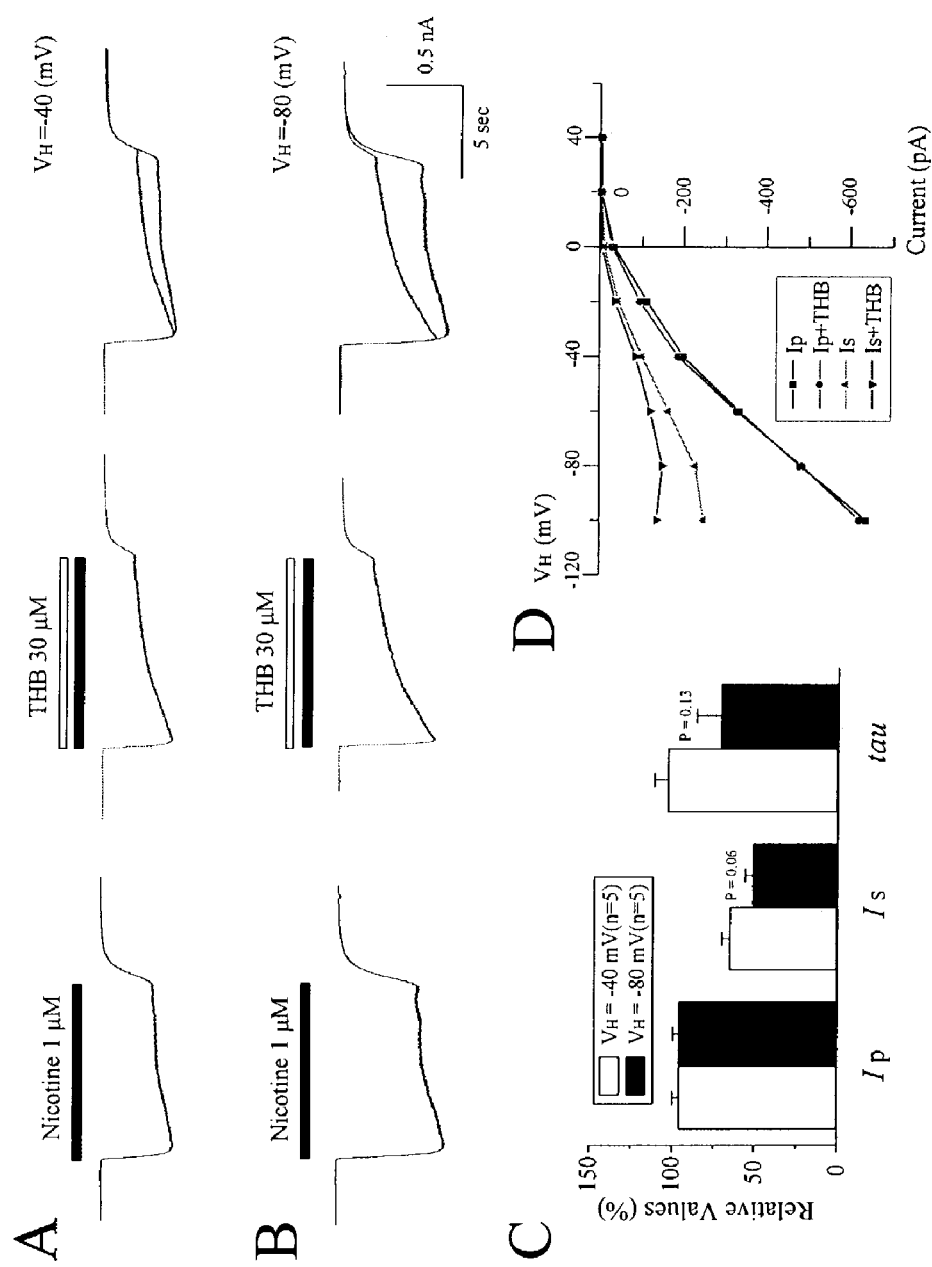
FIG. 9 illustrates how THB accelerates acute desensitization of nicotinic current.

Magnoliidae compounds also act on ion channels, such as calcium ($Ca^{2+}$) channels, potassium ($K^+$) channels, sodium ($Na^{2+}$) channels, or chloride ($Cl^-$) channels. For instance, FIG. 8 shows that Magnoliidae compound (THB) suppressed nicotinic response depending on $V_H$, meaning that THB may insert into nicotinic channel pores during nAChR activation to block these channels, termed 'open channel block' mechanism. 'Open channel block' may accelerate nAChR desensitization. The direct action of Magnoliidae compounds on $Ca^{2+}$ and $K^+$ channels, for example, also protects cardiac tissues and brain tissues against ischemia-induced injury.

Because of the manner in which Magnoliidae compounds act on biological mechanisms in the brain, as described above, Magnoliidae compounds can also be used in some neurological and psychological disorder treatment and prevention, for example, Alzheimer's Disease (AD) and Parkinson's Disease (PD). Specifically, co-administration of Magnoliidae compounds with levadopa (L-DOPA), as PD therapy, will prevent or significantly delay L-DOPA-induced akinesia. Furthermore, with the recent development of nicotinic agonists as a novel therapeutic strategy for both AD and PD, co-application of Magnoliidae compounds with low concentrations of the nicotinic agonists will increase efficacy and reduce the current side-effects that include nicotine tolerance and nicotine dependence. Finally, since midbrain DA receptor over-activity is the major cause of schizophrenia, the ability of Magnoliidae compounds to act as a DA receptor antagonist demonstrates that Magnoliidae compounds can be useful as an anti-schizophrenia agent.

According to clinical trial data, the optimal dosage to decrease nicotine use and produce smoking cessation is by administering a dose of 10-50 mg/Kg of body weight of one or more Magnoliidae compounds, including THB, 1-THP, 1-SPD, or any other THB analog, and the effects can be maintained for 2-3 hours. However, since Magnoliidae compounds easily pass the blood-brain barrier, they quickly and easily reach peak concentration in the brain tissue. Therefore, doses as low as 1 mg/Kg of body weight can cause nicotine-desensitization and decrease nicotine use.

Also because of the ease in passing the blood-brain barrier, administration of Magnoliidae compounds can be accomplished in several ways. It is important to note that administration of Magnoliidae compounds can occur either by administration of the Magnoliidae plant without purification or extraction of the Magnoliidae compounds, or by administration of the Magnoliidae compounds following extraction or purification. Therefore, administration of Magnoliidae described below includes both the extracted or purified Magnoliidae compounds, as well as the any part of a Magnoliidae plant.

Because Magnoliidae and Magnoliidae compounds are effective when ingested orally, numerous vehicles for delivery of Magnoliidae are possible. The method of administration of Magnoliidae can be by simply mixing it with the food the human is to consume, prepared in forms of capsules, tablets, powders, germ, liquids, shakes, bars, candies or other confections, tea bags, or chewing gum or any other form of food.

Furthermore, administration of Magnoliidae can be in liquid form. Magnoliidae can be administered as a drink including, but not limited to, soft drinks, coffee, tea, nutritional and dietary supplement drinks, milk shakes, and protein shakes. Magnoliidae can also be administered sublingually in a chewing gum form. The method of administration with the Magnoliidae can also be by integrating it into sprays or lozenges to deliver sublingually to by-pass liver metabolism.

The method of administration with the Magnoliidae compounds can also be by making the Magnoliidae plant capable of respiratory inhalation. For example, parts of the Magnoliidae plant can be made into a tobacco-free cigarette or cigar. Administration in this manner is particularly desirable for reducing nicotine use while not requiring withdrawal from the psychological and behavioral aspects of smoking.

Administration of Magnoliidae compounds can also be effectively accomplished by preparing the Magnoliidae compounds in injectable forms to deliver parenterally to by-pass liver metabolism and for faster and stronger actions. Magnoliidae compounds can be dissolved in injection solution and be prepared either for use as a subcutaneous injection or for use as a direct venous injection or in an intravenous solution.

Finally, Magnoliidae compounds can be made into a patch so that the Magnoliidae compounds can be administered by dermal application of the patch to the skin. A Magnoliidae compound patch can also be prepared with a nicotine additive, or other nicotine-replacement-therapy, for increased efficacy.

Various embodiments of the invention are described above in the Drawings and Description of Various Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out this invention, but that the invention will include all embodiments falling within the scope of the appended claims.

What is claimed is:

1. A method of attenuating nicotine withdrawal by desensitizing nicotinic acetyicholine receptors comprising the step of administering an effective amount of an extract from a *Corydalis, Stephania* or *Fibraurea* plant to a subject having or at risk of having nicotine withdrawal such that nicotinic acetylcholine receptors are desensitized.

2. A method as recited in claim 1, wherein the effective amount of the extract is greater than 1 mg/kg body weight.

3. A method as recited in claim 1, wherein the effective amount of the extract is about 10 mg/kg to about 50 mg/kg body weight.

4. A method as recited in claim 1, wherein the extract is from a plant part selected from the group consisting of leaves, stems and tubers.

5. A method as recited in claim 1, wherein the extract is from a tuber.

6. A method as recited in claim 1, wherein the extract is administered via a method selected from the group consisting of oral, sublingual, subcutaneous, topical, inhalation and intravenous.

7. A method as recited in claim 1, wherein the extract is administered in a food product.

8. A method as recited in claim 7, wherein the food product is chewing gum.

9. A method as recited in claim 1, wherein the extract is administered in a dermal patch.

10. A method as recited in claim 9, wherein the dermal patch further comprises nicotine.

11. A method as recited in claim 1, wherein the extract comprises a compound selected from the group consisting of tetrahydroberberine, l-tetrahydropalmatine, l-stepholidine and analogs thereof.

12. A method as recited in claim 11, wherein the analogs comprise a benzene-hexane-hexane-benzene structure.

13. A method as recited in claim 11, wherein the compounds are purified from the extract.

14. A method as recited in claim 1, wherein the nicotinic acetylcholine receptors are selected from the group consisting of $\alpha 4\beta 2$, $\alpha 4\beta 4$ and $\alpha 7$.

15. A method of reducing sensitization to nicotine by attenuating nicotine-induced dopamine release by nicotinic acetylcholine receptors comprising the step of administering an effective amount of an extract from a *Corydalis, Stephania* or *Fibraurea* plant to a subject having or at risk of having sensitization to nicotine, wherein the extract comprises a compound selected from the group consisting of tetrahydroberberine, l-tetrahydropalmatine, l-stepholidine and analogs thereof, such that nicotine-induced dopamine release is attenuated.

16. A method as recited in claim 15, wherein the effective amount of the extract is an amount greater than 1 mg/kg body weight.

17. A method of attenuating nicotine withdrawal by desensitizing nicotinic acetylcholine receptors comprising of the step of administering an effective amount of an extract consisting of a *Corydalis, Stephania* or *Fibraurea* plant to a subject having or at risk of having nicotine withdrawal such that nicotinic acetylcholine receptors are desensitized.

18. A method of reducing sensitization to nicotine by attenuating nicotine induced dopamine release by nicotinic acetylcholine receptors comprising the step of administering an effective amount of an extract from a *Corydalis, Stephania* or *Fibraurea* plant to a subject having or at risk of having sensitization to nicotine, wherein the extract consists of a compound selected from the group consisting of tetrahydroberberine, l-tetrahydropalmatine, l-stepholidine and analogs thereof, such that nicotine-induced dopamine release is attenuated.

* * * * *